US012691218B2

(12) United States Patent
Ellis et al.

(10) Patent No.: US 12,691,218 B2
(45) Date of Patent: Jul. 28, 2026

(54) APPARATUS AND METHODS OF CHEMICALLY-POWERED FLUID FLOW SYSTEMS

(71) Applicant: Battelle Memorial Institute, Columbus, OH (US)

(72) Inventors: Jeffrey L. Ellis, Columbus, OH (US); John P. Tallarico, Powell, OH (US); Jeffrey J. Boyce, Grove City, OH (US)

(73) Assignee: Battelle Memorial Institute, Columbus, OH (US)

( * ) Notice: Subject to any disclaimer, the term of this patent is extended or adjusted under 35 U.S.C. 154(b) by 1163 days.

(21) Appl. No.: 17/761,570

(22) PCT Filed: Sep. 23, 2020

(86) PCT No.: PCT/US2020/052259
§ 371 (c)(1),
(2) Date: Mar. 17, 2022

(87) PCT Pub. No.: WO2021/061802
PCT Pub. Date: Apr. 1, 2021

(65) Prior Publication Data
US 2022/0339351 A1 Oct. 27, 2022

Related U.S. Application Data

(60) Provisional application No. 62/904,630, filed on Sep. 23, 2019, provisional application No. 62/904,638, filed on Sep. 23, 2019.

(51) Int. Cl.
*A61M 5/155* (2006.01)
*A61M 5/20* (2006.01)
*A61M 5/142* (2006.01)

(52) U.S. Cl.
CPC .......... *A61M 5/155* (2013.01); *A61M 5/2046* (2013.01); *A61M 2005/14204* (2013.01)

(58) Field of Classification Search
None
See application file for complete search history.

(56) References Cited

U.S. PATENT DOCUMENTS 4,505,710 A * 3/1985 Collins ............. A61M 5/14276
604/131
5,318,540 A 6/1994 Athayde et al.
(Continued)

FOREIGN PATENT DOCUMENTS

WO 1998053866 A1 12/1998
WO WO-2014059444 A2 * 4/2014 .......... A61M 5/2046

OTHER PUBLICATIONS

First Office Action in European Patent Application No. EP20803674.9A dated Nov. 7, 2024.
(Continued)

*Primary Examiner* — Bhisma Mehta
*Assistant Examiner* — Haden Matthew Ritchie
(74) *Attorney, Agent, or Firm* — Susanne A. Wilson; Frank Rosenberg

(57) ABSTRACT

Processes and devices for delivering a fluid by decomposition of hydrogen peroxide are disclosed. Advantageously, the reaction is very fast and exothermic resulting in a fast ejection and, optionally, heating a fluid as it is ejected from a container. Also disclosed is a fluid flow system powered by a gas-generating reaction that is activated by an electrothermal activation switch.

11 Claims, 2 Drawing Sheets

(56)                    References Cited

U.S. PATENT DOCUMENTS

| | | | |
|---|---|---|---|
| 5,992,700 A | 11/1999 | McGlothlin et al. | |
| 8,113,390 B2 | 2/2012 | Wold | |
| 9,089,244 B2 | 7/2015 | Gray et al. | |
| 10,046,116 B2 | 8/2018 | Bennison et al. | |
| 2004/0073169 A1* | 4/2004 | Amisar ................. | A61M 5/155 604/141 |
| 2019/0307954 A1* | 10/2019 | Klemm ................. | A61M 5/155 |

OTHER PUBLICATIONS

International Preliminary Report on Patentability from International Application No. PCT/US2020/052259 dated Mar. 15, 2022.
Written Opinion of the International Search Authority from International Application No. PCT/US2020/052259 date of mailing Mar. 31, 2021.
International Search Report from International Application No. PCT/US2020/052259 date of mailing Mar. 31, 2021.
Zizzari et al: "Self-powered catalytic microfluidic platforms for fluid delivery", Colloids and Surfaces A: Physicochemical and Engineering Aspects, 532 (2017), pp. 257-262.

* cited by examiner

Initial / Storage           Activated

APPARATUS AND METHODS OF CHEMICALLY-POWERED FLUID FLOW SYSTEMS

RELATED APPLICATIONS

This application is a U.S. National Stage application of International Application No. PCT/US2020/052259, filed 23 Sep. 2020, and claims the benefit of priority of U.S. provisional applications Nos. 62/904,638 and 62/904,630 which were both filed 23 Sep. 2019.

INTRODUCTION

The invention described in this patent application arose from the need for improved methods of delivering of fluids in the field of medicine.

The displacement of fluids from containers has been an active area of study since at least the time of Archimedes over 2000 years ago. Hydrogen peroxide ($H_2O_2$) was first isolated over 200 years ago and shortly thereafter, it was found to decompose to produce oxygen gas ($O_2$). In the present invention, these two ancient concepts are utilized to control the delivery of fluids in new ways, especially in the field of medicine, where these fundamental concepts are utilized to improve the lives of patients.

As described in greater detail below, the present invention relates to the use of hydrogen peroxide to displace fluids from containers, and one particularly preferred application is the parenteral delivery of high-viscosity fluids, e.g., protein therapeutics, where the decomposition of hydrogen peroxide is used to drive a fluid and/or warm a composition. A variety of parenteral delivery systems are described in Bennison et al., U.S. Pat. No. 10,046,116 which is incorporated herein as if reproduced in full below. Although Bennison et al. provide examples using sodium bicarbonate, they do mention that "hydrogen peroxide can be decomposed with catalysts such as enzymes (e.g. catalase) or manganese dioxide to produce oxygen gas."

The use of the decomposition of hydrogen peroxide to deliver fluids has been described previously in certain contexts. See, for example, Zizzari et al. in "Self-powered catalytic microfluidic platforms for fluid delivery," Colloids and Surfaces A 532 (2017) 257-262 focus on microfluidic platforms in the lab-on-chip field using flexible thin membranes made of poly(dimethylsiloxane) in which $H_2O_2$ dismutation occurs in the presence of a $Na_{10}[Ru_4O_4(OH)_2 (H_2O)_4(\gamma\text{-}SiW_{10}O_{36})_2]$ catalyst. McGlothlin et al, in U.S. Pat. No. 5,992,700 mentions that an aqueous peroxide solution can be wicked into a catalyst to prolong the rate of gas generation. Gray et al. U.S. Pat. No. 9,089,244 discloses a dispenser that is powered by the decomposition of hydrogen peroxide that is catalyzed by manganese dioxide, platinum or a mesh having a silver coating.

The present invention also concerns the problems of activating fluid delivery systems that are powered by a chemical reaction. Conventionally, in chemically-powered fluid delivery systems such as autoinjectors and the like, the chemical reaction is activated by mechanical means such as opening a valve or breaking a barrier. A variety of conventional, chemically-powered fluid delivery systems are described in Bennison et al., U.S. Pat. No. 10,046,116 which is incorporated herein as if reproduced in full below. A problem with the conventional activation systems is that some disabled people have difficulty handling mechanical activation systems and, furthermore, the need for mechanical activation structures can limit the construction of the fluid-delivery device in ways that an electrically-activated system would not.

The present invention provides novel systems, apparatus and methods that utilize the decomposition of hydrogen peroxide in advantageous ways to deliver a fluid.

SUMMARY

In several aspects, the invention provides devices, methods, and systems for delivery of fluids powered by the decomposition of hydrogen peroxide. In one aspect, the invention provides a device for delivering a fluid by decomposition of hydrogen peroxide, comprising: a catalyst chamber comprising a $H_2O_2$ decomposition catalyst; a hydrogen peroxide chamber comprising an aqueous solution of hydrogen peroxide; wherein the solids catalyst chamber or the hydrogen peroxide chamber comprises a reaction chamber; a frangible (meaning breakable under the reaction conditions) barrier or valve separating the catalyst and the hydrogen peroxide solution; a fluid chamber comprising a fluid or a meltable solid; a thermally conductive wall separating the reaction chamber from the fluid chamber; a plunger (as defined in the Glossary) that moves in response to pressure generated in the reaction chamber such that the volume of the reaction chamber increases and the volume of the fluid chamber decreases; wherein the fluid chamber comprises an orifice such that fluid forced out of the fluid chamber can pass through the orifice. Note that there may be several orifices connected to the fluid chamber but in preferred embodiments there is a single orifice. The device may contain multiple fluid chambers, preferably with one orifice connected to each; the fluid(s) in plural fluid chambers can be forced out by hydrogen peroxide decomposition in a single reaction chamber; or the device may comprise plural reaction chambers, each connected to a single or to plural fluid chambers. In some embodiments, only a portion of the wall that separates the reaction chamber from the fluid chamber is thermally conductive. In some preferred embodiments, the relative amounts of $H_2O_2$ and fluid are sized such that the decomposition of the $H_2O_2$, assuming that 100% of the heat of reaction is consumed in heating the $H_2O_2$ product solution and heating the substance in the fluid chamber and assuming that the substance in the fluid chamber starts at 5° C., will raise the temperature of the substance in the fluid chamber by at least 5° C., or at least 10° C., or in the range of 5 to 40° C., or 10 to 30° C.

In many embodiments, the orifice is connected to a nozzle and the fluid passes through the nozzle and then through a needle that is connected to the nozzle. In an alternate embodiment, the device is configured with only a thermally conductive wall separating the reaction chamber from the nozzle—in this case heat from the reaction is focused on fluid in the nozzle. In some embodiments, the orifice connects to a nozzle having a length of at least 0.5 cm and wherein the reaction chamber is disposed around the nozzle and the thermally conductive wall is disposed around the nozzle.

In some preferred embodiments, the wall separating the reaction chamber from the fluid chamber has a higher thermal conductivity than another reaction chamber wall or portion of reaction chamber wall that does not separate the reaction chamber from the fluid chamber. In some embodiments, the ratio of the surface area of the wall separating the reaction chamber from the fluid chamber (only the portion of the wall that is in direct contact with the fluid chamber) to the volume of the fluid chamber is from 0.1 to 10, or 0.5 to 5, or 1.0 to 3 cm²/cc. In some embodiments, except for the thermally conductive wall, the walls of the reaction chamber (and optionally the walls of the fluid chamber) comprise materials (typically a single material) that have a low heat capacity of 0.5 or less or 0.4 or less, or 0.3 or less cal/g° C. (measured at standard temperature and pressure) and/or a thermal conductivity that is at least 10% less than the conductivity of the thermally conductive wall (or at least 50% less) at 25° C. Typically, these walls are made of a polymer.

The invention also includes systems comprising any of the devices described herein. Preferably, the substance in the fluid chamber is at a temperature of 0 to 80° C. Any of the devices or systems may further comprise a time-delay release on the fluid chamber. One way that a time delay can be implemented is installation of a pressure release feature between the reaction chamber and the fluid chamber. The reaction will be initiated, it will evolve heat, and the pressure will increase until a specified release feature (burst disc, relief valve, viscous grease in capillary) allows the pressure to pass from the reaction chamber to the fluid chamber plunger. In a different embodiment, the plunger could be anchored in place by mechanical means. Once a specified pressure is reached in the reaction chamber, it applies sufficient force to break the mechanical linkage and allows the plunger to move freely. In some preferred embodiments, the time delay release is a valve or frangible barrier disposed at the orifice.

In another aspect, the invention provides a method of delivering a fluid, comprising: providing a device comprising: a reaction chamber and a fluid chamber; wherein the fluid chamber comprises a fluid or a meltable solid; a thermally conductive wall separating the reaction chamber from the fluid chamber; a plunger that moves in response to pressure generated in the reaction chamber such that the volume of the reaction chamber increases and the volume of the fluid chamber decreases; wherein the fluid chamber comprises an orifice such that fluid forced out of the fluid chamber can pass through the orifice; in the reaction chamber, combining hydrogen peroxide with a $H_2O_2$ decomposition catalyst wherein oxygen gas and heat are generated (or combining liquid reactants (or combining a liquid reactant with a solid reactant) that exothermically react to generate a gas); wherein heat from the reaction chamber is transferred to the fluid or meltable solid in the fluid chamber; wherein the oxygen gas produced in the reaction chamber increases pressure inside the reaction chamber and moves the plunger which in turn forces fluid from the fluid chamber. In some preferred embodiments, at least 10%, or at least 20%, or at least 30%, or at least 40%, or at least 50%, or at least 60%, or from 20 to 80% of the heat generated in the reaction chamber is transferred to the substance in the fluid chamber. In some embodiments, the fluid or meltable solid in the fluid chamber is in the range of 0 to 10 C at the start of the method, and is at a temperature of between 15 and 40 C or 15 to 35 C as it exits from the orifice or nozzle. In some embodiments, the fluid chamber comprises a solid that melts or a viscous fluid that changes to a less viscous fluid as a result of heat released from the reaction chamber, wherein the melted solid or less viscous fluid passes through the orifice and out of the device, and then cools and changes to a solid or a fluid with a higher viscosity than the fluid that passes through the orifice. The fluid chamber may comprise a fluid that absorbs heat from the reaction chamber and, as a result, decreases in viscosity. In some preferred embodiments, the fluid decreases in viscosity by at least 10%, 20%, 50%, or at least 70%, or from 10 to 90%.

In a further aspect, the invention provides a device for delivering a fluid by decomposition of hydrogen peroxide, comprising: a barrel containing a reaction chamber and a fluid chamber which are separated by a moveable piston; wherein, prior to use, the reaction chamber comprises separate chambers for catalyst and hydrogen peroxide, and the fluid chamber comprises a fluid; a thermally conductive element that is adapted to transfer heat from the reaction chamber to the fluid. The thermally conductive element could be a metalized foil layer on the reactant pouch, a highly filled polymer resin (for example, Celanese Coolpoly has thermal conductivity up to 40 W/mK), doped glass, or a metallic part.

The invention also includes a process for delivering a high-viscosity fluid by decomposition of hydrogen peroxide, comprising use of the any of the devices described herein.

In another aspect, the invention provides a device for delivering a fluid by decomposition of hydrogen peroxide, comprising: a solids catalyst chamber comprising a metal oxide powder catalyst and a soluble catalyst; a hydrogen peroxide chamber; wherein the solids catalyst chamber or the hydrogen peroxide chamber comprises a reaction chamber; a frangible barrier or valve separating the catalyst and hydrogen peroxide; a fluid chamber comprising a fluid; a piston that moves in response to pressure generated in the reaction chamber such that the volume of the reaction chamber increases and the volume of the fluid chamber decrease. In some embodiments, the hydrogen peroxide chamber comprises a plunger at an upper end and a one-way valve at a lower end, the one-way valve permitting exit from the hydrogen peroxide chamber; the solids catalyst chamber having the one-way valve at an upper end and a piston at a lower end; and the fluid chamber having the piston at an upper end, wherein the piston moves in response to pressure generated in the solids catalyst chamber such that the volume of the solids catalyst chamber increases and the volume of the fluid chamber decreases. In some preferred embodiments, the metal oxide powder catalyst manganese dioxide, copper(II) oxide, zinc oxide, and combinations thereof. In some embodiments, the soluble catalyst comprises iron(III) chloride, copper(II) sulfate, potassium iodide, and combinations thereof.

In any of the inventive aspects, the devices, methods or systems can be characterized by one or more of the following characteristics: the reaction chamber has a volume of at most 20 cm³ or 10 cm³ or 5 cm³ or at most 1.5 cm³, in some embodiments at most 1.0 cm³; the fluid chamber contains a high-viscosity fluid having an absolute viscosity of from about 5 centipoise to about 50,000 centipoise, or an absolute viscosity of at least 20, preferably at least 40 centipoise, in some embodiments in the range of 20 to 100 cP. Unless specified to the contrary, absolute viscosity refers to viscosity at 20° C. In some preferred embodiments, the fluid chamber contains a high-viscosity fluid having a viscosity of at least 40 centipoise. In some embodiments, the fluid chamber comprises a meltable solid. In some embodiments, the substance in the fluid chamber is a thixotropic fluid. In some preferred embodiments, the reaction chamber and the fluid chamber are adjacent in the housing.

The present disclosure also relates to devices for delivering a fluid by chemical reaction, comprising: a reaction chamber divided by a barrier into a first compartment and a second compartment, the first compartment containing one or more dry catalysts (and/or a first reagent), and the second compartment containing $H_2O_2$ (or other reagent); and a fluid chamber having an outlet; wherein fluid in the fluid chamber exits through the outlet in response to pressure generated in the reaction chamber. In the case of solid sodium percarbonate, the hydroxide is in the reaction chamber and a liquid catalyst flows into the reaction chamber while this order is typically reversed in the case of liquid hydrogen peroxide and solid catalyst.

In another aspect, the invention comprises a first chamber comprising $H_2O_2$; and a second chamber may contain at least one catalyst that catalyzes the decomposition of $H_2O_2$. The device will typically have an initiation (also called activation) switch that may be mechanical or electronic. The pressure generated in a reaction chamber may act on a piston or plunger at one end of the fluid chamber to cause fluid to exit through the outlet of the fluid chamber. In some embodiments, the reaction chamber includes a flexible wall, proximate to the fluid chamber; and wherein the fluid chamber is formed from a flexible sidewall, such that pressure generated in the reaction chamber causes the flexible wall to expand and compress the volume of the fluid chamber, thus pushing fluid to exit through the outlet. The reaction chamber and the fluid chamber may be surrounded by a housing. Sometimes, the reaction chamber and the fluid chamber are side-by-side in the housing. In other embodiments, a needle extends from a bottom of the housing and is fluidly connected to the outlet of the fluid chamber; and the reaction chamber is located on top of the fluid chamber.

In another method of the invention, a switch is activated that allows an electric current to flow through a resistive heater that becomes hot and melts or decomposes a barrier material that opens a pathway between a reagent chamber and a reaction chamber. Fluid from the reagent chamber then flows into the reaction chamber wherein a gas generating reaction occurs to provide pressure to move a fluid in a device; for example, to force a fluid from a fluid delivery device. The device can be activated from a button or switch on the device; alternatively, it can be remotely or autonomously (sensor driven) activated through circuitry.

In a further aspect, the invention provides a fluid flow system, comprising: an activation switch; an electrical power source connected to the activation switch; a resistive heater attached to a first chamber; an electrical connection from the power source to the resistive heater; wherein the first chamber comprises a first reaction composition; a second chamber comprising a second reaction composition; wherein, if the first and second reaction compositions are combined, a gas is generated; wherein the resistive heater is adapted to open a pathway in the first chamber that creates an open flow path between the first and second chambers; the first chamber comprising at least one collapsible wall; a fluid chamber comprising a fluid; and a plunger adjacent the fluid chamber that is adapted to reduce volume of the fluid chamber when the gas is generated.

Collapsible means that at least a portion of a wall (up to the all the walls of the chamber) are deformable such that the chamber can reduce in volume as a composition within the chamber is expelled. The collapsible wall assists in expulsion of the first reaction composition from the first reaction chamber. Over the course of reaction, the internal volume of the first chamber reduces in volume by at least 20%, or at least 50%, or at least 95%, or 50 to 100%. The first chamber can be made of a meltable material such as a polymeric film; alternatively, the first chamber can be comprised of an elastic material (that itself is not necessarily meltable but comprises a valve that melts or decomposes in response to the heat supplied by the resistive heater). The valve can be, for example, a simple plug or patch of material that opens a pathway between the first and second chambers allowing the first and second compositions to mix together and react;

typically, the gas generating reaction squeezes (applies pressure to) the first chamber that cause the first composition to be further expelled into the reaction chamber.

Typically, the plunger is disposed between an expansion chamber (in some preferred embodiments, the reaction chamber) and the fluid chamber. In some embodiments, the first and second reaction compositions are fluid compositions that flow into an expansion chamber. In an alternative embodiment, the first chamber is the expansion chamber; alternatively, the second chamber may be the expansion chamber. The first and second reaction compositions may each comprise one or more reactants and, optionally, a catalyst; or one reaction composition may comprise a catalyst while the other composition comprises a compound (such as hydrogen peroxide) that decomposes in the presence of the catalyst. The first chamber may be comprised of a stretched material that contracts as fluid is ejected from the chamber; in another alternative, one or more springs can push against the first chamber. In some embodiments, a single device may comprise a plurality (for example, at least 2 or at least 5, or from 2 to 100) of first chambers (either connected to a single second chamber or a plurality of second chambers) wherein each first chamber comprises a resistive heater adapted to open a pathway in the first chamber; the resistive heaters can be heated simultaneously or individually addressed either manually, or more typically, in an automated fashion.

In a further aspect, the invention provides novel systems, apparatus and methods that utilize electrothermal activation of a chemically-powered fluid flow system. Throughout the descriptions herein, the catalyzed decomposition of hydrogen peroxide is used as the example of gas-generating reaction; however, it should be understood that the invention operates well with other gas-generating reactions and the descriptions should be understood as being generally applicable to any gas-generating reaction in which two materials are combined to result in a gas-generating reaction.

The invention also includes a process for delivering a high-viscosity fluid by initiating a gas-generating reaction, comprising use of the any of the devices described herein.

The invention includes apparatus, systems, and methods. The apparatus can be described in terms of structural features, solid and fluid substances, and functional features. Systems are similar to apparatuses and may include temperature descriptions and conditions. Any of the inventive aspects should be understood, in optional embodiments, to include any of the features described herein. Many aspects of the invention are described in conjunction with the term "comprising" which means including; in any of these aspects, the invention also includes narrower embodiments characterized by the term "consisting essentially of" or "consisting of" in place of "comprising" given the conventional meaning of these terms in patent law.

GLOSSARY

Figures 1, 4:
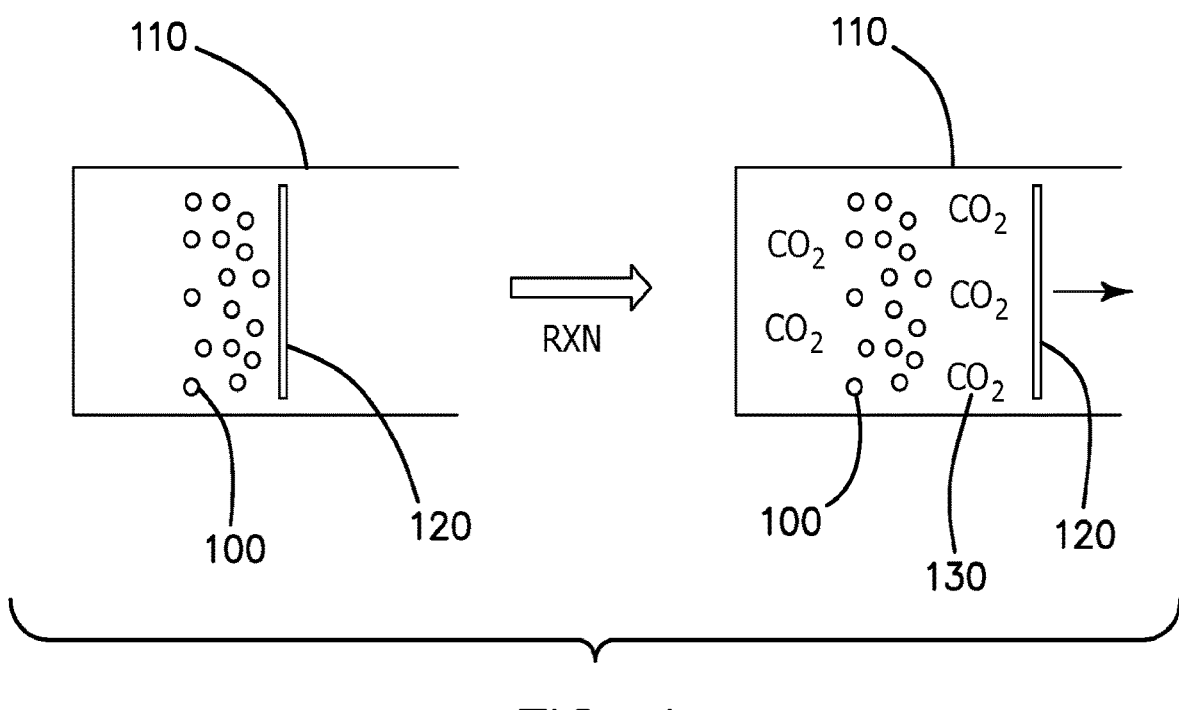
FIG. 1 illustrates the general principle of expansion from a gas generating reaction. Although the figure shows $CO_2$, it should be recognized that the decomposition of $H_2O_2$ forms $H_2O$ and $O_2$.
FIG. 4 schematically illustrates a pouch squeezing dispenser.

An activation switch is a mechanical or electronic mechanism that initiates the combination of reactants that initiates the decomposition reaction. The device can be operated from a button or switch on the device; alternatively, it can be remotely or autonomously (sensor driven) activated through circuitry.

A "fluid dispenser" is a device that, when activated, ejects a fluid through one or more orifices. A "fluid flow system" is any device in which activation causes the movement of fluid in the device; this includes, for example, fluid delivery systems as well as systems in which fluid is propelled through a device such as an enzyme-linked immunosorbent assay (ELISA).

It should be noted that many of the terms used herein are relative terms. For example, the terms "inlet" and "outlet" are relative to a direction of flow, and should not be construed as requiring a particular orientation or location of the structure. Similarly, the terms "upper" and "lower", and "top" and "bottom", are relative to a central point. For example, an upper component is located in one direction from the central point and a lower component would be located in the opposite direction from the central point.

A "liquid" is a substance that flows under the influence of gravity or a small amount of pressure (up to 5 atm).

A "meltable solid", for purposes of the present invention, is an aqueous solution that melts near 0° C., or a biological, organic (meaning carbon-based), or polymeric composition that transitions between a solid and a liquid.

An orifice is any opening, an orifice can have an attached neck or nozzle.

The term "parenteral" refers to a delivery means that is not through the gastrointestinal tract, such as injection or infusion.

A plunger (also called an "expansion plunger") is any component that moves or deforms in response to $H_2O_2$ generated in the chemical engine and which can transmit force, either directly or indirectly, to a liquid in a compartment that is either adjacent to or indirectly connected to the chemical engine. For example, the plunger could push against a piston that, in turn, pushes against a liquid in a syringe. There are numerous types of plungers described in this application and in the prior art, and the inventive formulations and designs are generally applicable to a multitude of plunger types. The plunger may or may not form a seal on the reaction chamber.

An initiation plunger is a moveable part that is used to initiate a reaction, usually by directly or indirectly causing the combination of hydrogen peroxide and catalyst. Preferably, the initiation plunger locks into place to prevent any loss of pressure and thus direct all the generated pressure toward the fluid to be ejected from the fluid chamber.

A "protein" is a sequence of amino acids that is of sufficient chain length to produce a tertiary or quaternary structure. Examples of proteins include monoclonal antibodies, insulin, human growth hormone, and erythropoietin.

A "thermally conductive wall" is a wall having a thermal conductivity of at least 0.2 W/(mK) (watt per meter Kelvin) at 25° C. More preferably at least 0.5, more preferably at least 1, more preferably at least 2, and in some embodiments the wall is metallic.

Viscosity can be defined in two ways: "kinematic viscosity" or "absolute viscosity." Kinematic viscosity is a measure of the resistive flow of a fluid under an applied force. The SI unit of kinematic viscosity is $mm^2/sec$, which is 1 centistoke (cSt). Absolute viscosity, sometimes called dynamic or simple viscosity, is the product of kinematic viscosity and fluid density. The SI unit of absolute viscosity is the millipascal-second (mPa-sec) or centipoise (cP), where 1 cP=1 mPa-sec. Unless specified otherwise, the term viscosity always refers to absolute viscosity. Absolute viscosity can be measured by capillary rheometer, cone and plate rheometer, or any other known method.

The processes of the present disclosure can be used with both manual syringes, auto-injectors, or other fluid dispensers and is not limited to cylindrical geometries. The term "syringe" is used interchangeably to refer to manual syringes and auto-injectors of any size or shape. The term "injection device" is used to refer to any device that can be used to inject the fluid into a patient, including for example syringes and patch pumps.

Various aspects of the invention are described using the term "comprising;" however, in narrower embodiments, the invention may alternatively be described using the terms "consisting essentially of" or, more narrowly, "consisting of."

DETAILED DESCRIPTION

In one aspect, the invention provides a device for delivering a fluid by decomposition of hydrogen peroxide, comprising: a catalyst chamber (a first chamber) comprising a $H_2O_2$ decomposition catalyst; a hydrogen peroxide chamber (a second chamber) comprising an aqueous solution of hydrogen peroxide; wherein the solids catalyst chamber or the hydrogen peroxide chamber comprises a reaction chamber; a heat-activatable barrier or valve separating the catalyst and the hydrogen peroxide solution; a fluid chamber comprising a fluid or a meltable solid; a thermally conductive wall separating the reaction chamber from the fluid chamber; a plunger (as defined in the Glossary) that moves in response to pressure generated in the reaction chamber such that the volume of the reaction chamber increases and the volume of the fluid chamber decreases; wherein the fluid chamber comprises an orifice such that fluid forced out of the fluid chamber can pass through the orifice. Note that there may be several orifices connected to the fluid chamber but in preferred embodiments there is a single orifice. The device may contain multiple fluid chambers, preferably with one orifice connected to each; the fluid(s) in plural fluid chambers can be forced out by hydrogen peroxide decomposition in a single reaction chamber; or the device may comprise plural reaction chambers, each connected to a single or to plural fluid chambers. In some embodiments, only a portion of the wall that separates the reaction chamber from the fluid chamber is thermally conductive. In some preferred embodiments, the relative amounts of $H_2O_2$ and fluid are sized such that the decomposition of the $H_2O_2$, assuming that 100% of the heat of reaction is consumed in heating the $H_2O_2$ product solution and heating the substance in the fluid chamber and assuming that the substance in the fluid chamber starts at 5° C., will raise the temperature of the substance in the fluid chamber by at least 5° C., or at least 10° C., or in the range of 5 to 40° C., or 10 to 30° C.

In many embodiments, the orifice is connected to a nozzle and the fluid passes through the nozzle and then through a needle that is connected to the nozzle. In an alternate embodiment, the device is configured with only a thermally conductive wall separating the reaction chamber from the nozzle—in this case heat from the reaction is focused on fluid in the nozzle. In some embodiments, the orifice connects to a nozzle having a length of at least 0.5 cm and wherein the reaction chamber is disposed around the nozzle and the thermally conductive wall is disposed around the nozzle.

In some preferred embodiments, the wall separating the reaction chamber from the fluid chamber has a higher thermal conductivity than another reaction chamber wall or portion of reaction chamber wall that does not separate the reaction chamber from the fluid chamber. In some embodiments, the ratio of the surface area of the wall separating the reaction chamber from the fluid chamber (only the portion of the wall that is in direct contact with the fluid chamber) to the volume of the fluid chamber is from 0.1 to 10, or 0.5 to 5, or 1.0 to 3 cm²/cc. In some embodiments, except for the thermally conductive wall, the walls of the reaction chamber (and optionally the walls of the fluid chamber) comprise materials (typically a single material) that have a low heat capacity of 0.5 or less or 0.4 or less, or 0.3 or less cal/g° C. (measured at standard temperature and pressure) and/or a thermal conductivity that is at least 10% less than the conductivity of the thermally conductive wall (or at least 50% less) at 25° C. Typically, these walls are made of a polymer.

The invention also includes systems comprising any of the devices described herein. Preferably, the substance in the fluid chamber is at a temperature of 0 to 80° C. Any of the devices or systems may further comprise a time-delay release on the fluid chamber. One way that a time delay can be implemented is installation of a pressure release feature between the reaction chamber and the fluid chamber. The reaction will be initiated, it will evolve heat, and the pressure will increase until a specified release feature (burst disc, relief valve, viscous grease in capillary) allows the pressure to pass from the reaction chamber to the fluid chamber plunger. In a different embodiment, the plunger could be anchored in place by mechanical means. Once a specified pressure is reached in the reaction chamber, it applies sufficient force to break the mechanical linkage and allows the plunger to move freely. In some preferred embodiments, the time delay release is a valve or frangible barrier disposed at the orifice.

In another aspect, the invention provides a method of delivering a fluid, comprising: providing a device comprising: a reaction chamber and a fluid chamber; wherein the fluid chamber comprises a fluid or a meltable solid; a thermally conductive wall separating the reaction chamber from the fluid chamber; a plunger that moves in response to pressure generated in the reaction chamber such that the volume of the reaction chamber increases and the volume of the fluid chamber decreases; wherein the fluid chamber comprises an orifice such that fluid forced out of the fluid chamber can pass through the orifice; in the reaction chamber, combining hydrogen peroxide with a $H_2O_2$ decomposition catalyst wherein oxygen gas and heat are generated (or combining liquid reactants (or combining a liquid reactant with a solid reactant) that exothermically react to generate a gas); wherein heat from the reaction chamber is transferred to the fluid or meltable solid in the fluid chamber; wherein the oxygen gas produced in the reaction chamber increases pressure inside the reaction chamber and moves the plunger which in turn forces fluid from the fluid chamber. In some preferred embodiments, at least 10%, or at least 20%, or at least 30%, or at least 40%, or at least 50%, or at least 60%, or from 20 to 80% of the heat generated in the reaction chamber is transferred to the substance in the fluid chamber. In some embodiments, the fluid or meltable solid in the fluid chamber is in the range of 0 to 10 C at the start of the method, and is at a temperature of between 15 and 40 C or 15 to 35 C as it exits from the orifice or nozzle. In some embodiments, the fluid chamber comprises a solid that melts or a viscous fluid that changes to a less viscous fluid as a result of heat released from the reaction chamber, wherein the melted solid or less viscous fluid passes through the orifice and out of the device, and then cools and changes to a solid or a fluid with a higher viscosity than the fluid that passes through the orifice. The fluid chamber may comprise a fluid that absorbs heat from the reaction chamber and, as a result, decreases in viscosity. In some preferred embodiments, the fluid decreases in viscosity by at least 10%, 20%, 30%, or at least 50%, or from 10 to 60%.

A device for delivering a fluid by decomposition of hydrogen peroxide, comprising: a barrel containing a reaction chamber and a fluid chamber which are separated by a moveable piston; wherein, prior to use, the reaction chamber comprises separate chambers for catalyst and hydrogen peroxide, and the fluid chamber comprises a fluid; a thermally conductive element that is adapted to transfer heat from the reaction chamber to the fluid. The thermally conductive element could be a metalized foil layer on the reactant pouch, a highly filled polymer resin (for example, Celanese Coolpoly has thermal conductivity up to 40 W/mK), doped glass, or a metallic part.

The fluid delivery devices may include a piston comprising a push surface at the lower end of the reaction chamber, a stopper at the upper end of the fluid chamber, and a rod connecting the push surface and the stopper. This is typically an injection-type configuration. A piston is one type of plunger. Any of the fluid delivery devices may comprise a power source (typically a battery), wires or other electrical connector, and a resistive heater that opens a pathway such that a reactive solution can flow into a reaction chamber, and a switch that can connect the resistive heater to the power source.

The fluid delivery devices may include a piston comprising a push surface at the lower end of the reaction chamber, a stopper at the upper end of the fluid chamber, and a rod connecting the push surface and the stopper. This is typically an injection-type configuration. A piston is one type of plunger. A plunger may include a thumbrest, as well as a pressure lock that cooperates with the upper chamber to lock the plunger in place after being depressed. The pressure lock can be proximate the thumbrest and cooperate with an upper surface of the upper chamber. A plunger that includes a thumbrest can be termed an initiation plunger since it frequently is employed to cause mixing to occur in which hydrogen peroxide and a decomposition catalyst are combined in solution.

In some embodiments, a chemical engine may comprise a lower chamber defined by the one-way valve, a continuous sidewall, and a piston, the one-way valve and the sidewall being fixed relative to each other such that the volume of the lower chamber changes only through movement of the piston.

In preferred embodiments, an upper chamber, lower chamber, and fluid chamber are cylindrical and are coaxial. The upper chamber, the lower chamber, and the fluid chamber can be separate pieces that are joined together to make the device. A one-way valve can feed a balloon in the lower chamber, the balloon pushing against the volume of the fluid chamber or against a piston.

A reaction chamber may be defined by the one-way valve, a sidewall, and a plunger, the one-way valve and the sidewall being fixed relative to each other such that the volume of the reaction chamber changes only through movement of the plunger.

Also disclosed in various embodiments is a device for dispensing a fluid by chemical reaction, comprising: a reaction chamber having first and second ends; a plunger at a first end of the reaction chamber, the plunger being operative to move within the device in response to a pressure generated in the reaction chamber; and a one-way valve at the second end of the reaction chamber permitting entry into the reaction chamber.

The device may comprise a reagent chamber on an opposite side of a one-way valve. The reagent chamber may contain hydrogen peroxide or may contain one or more hydrogen decomposition catalysts. The device may further comprise a plunger at an end of the reagent chamber opposite the one-way valve. The plunger may cooperate with the reagent chamber to lock an initiation plunger in place after being depressed.

Also disclosed in various embodiments is a device for delivering a fluid by chemical reaction, comprising: a barrel which is divided into a reagent chamber, a reaction chamber, and a fluid chamber by a one-way valve and a piston (or other type of plunger); and an initiation plunger at one end of the reagent chamber; wherein the one-way valve is located between the reagent chamber and the reaction chamber; and wherein the piston separates the reaction chamber and the fluid chamber, the piston (or other type of plunger) being moveable to change the volume ratio between the reaction chamber and the fluid chamber.

FIG. 1 illustrates the generation of pressure by a chemical reaction for use in powering the transfer of a fluid by from a container. Referring to the left hand side of the figures, one or more chemical reagents 100 are enclosed within a reaction chamber 110. One side of the chamber can move relative to the other sides of the chamber, and acts as a piston 120. The chamber 110 has a first volume prior to the chemical reaction.

A chemical reaction is then initiated within the chamber, as indicated by the "RXN" arrow. A gaseous byproduct 130 is generated. The volume of the chamber 110 remains fixed until the additional force generated by the gas pressure on the piston 120 exceeds that needed to push the fluid in the direction indicated by the arrow. The drawing shows $CO_2$, but in the case of hydrogen peroxide, the driving gases are $O_2$ and $H_2O$. The viscosity of the fluid can be approximated using the Hagen-Poiseuille equation. The Hagen-Poiseuille equation can predict the mass flow rate of a fluid based on its viscosity, the size orifice it must traverse, and the pressure evolved by the chemical reaction.

Once the minimum pressure required to move the piston 120 is exceeded, the volume of the reaction chamber 110 begins to increase. The movement of the piston 120 causes delivery of fluid within the container to begin. The pressure in the chamber 110 depends on both the rate of reaction and the rate of volume expansion, as represented by Equation (1). Preferably, sufficient gas is generated to account for the volume expansion, while not generating too much excess pressure. This can be accomplished by controlling the amount of $H_2O_2$.

The pressure build-up from the chemical-reaction produced gaseous product 130 can be used to push fluid directly adjacent to the piston 120 through the container (the container is a syringe in preferred embodiments). Pressure build-up may also push fluid in an indirect fashion, e.g., by establishing a mechanical contact between the piston 120 and the fluid, for example by a rod or shaft connecting the piston 120 to a stopper of a prefilled syringe that contains fluid.

One aspect of the present disclosure is the combination of various components to result in (i) enough force to deliver a viscous fluid in a short time period and (ii) in a small package that is compatible with the intended use, i.e. driving a syringe. In time, size, and in force must all come together to achieve the desired propulsion.

The shape of the reaction chamber can affect how accumulated pressure acts on the piston. In particular embodiments, the volume of the reaction chamber is 1 $cm^3$ or less. The other components of the device can be dimensioned to match the volume of the reaction chamber. A reaction chamber no more than 1 $cm^3$ allows enables chemical-reaction delivery of a high-viscosity fluid with a limited injection space or footprint.

Figure 2:
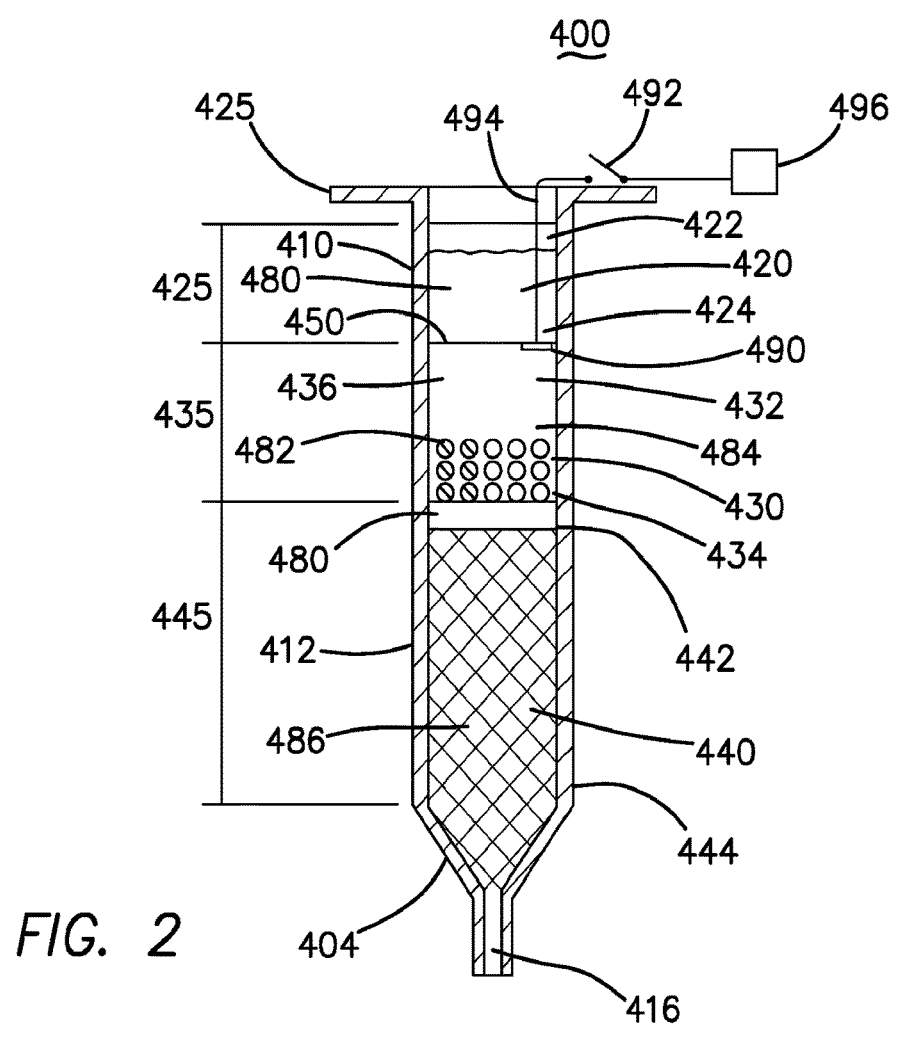
FIG. 2 illustrates one embodiment of an injector according to the present invention.

FIG. 2 illustrates one exemplary embodiment of a device (here, a syringe) that can be used to deliver a high-viscosity fluid using a chemical reaction between reagents to generate a gas. The syringe 400 is depicted here in a storage state or a non-depressed state in which the chemical reaction has not yet been initiated. The needle is not included in this illustration.

The syringe 400 includes a barrel 410 that is formed from a sidewall 412, and the interior space is divided into three separate chambers. Beginning at the top end 402 of the barrel, the syringe includes a reagent chamber 420, a reaction chamber 430, and a fluid chamber 440. The plunger 470 is inserted into an upper end 422 of the reagent chamber. A one-way valve 450 is present at a lower end 424 of the reagent chamber, forming a radial surface. The one-way valve 450 is also present at the upper end 432 of the reaction chamber. The one-way valve 450 is directed to permit material to exit the reagent chamber 420 and to enter the reaction chamber 430. The lower end 434 of the reaction chamber is formed by a piston 460. Finally, the piston 460 is present at the upper end 442 of the fluid chamber. The orifice 416 of the barrel is at the lower end 444 of the fluid chamber, and at the bottom end 404 of the syringe. It should be noted that the one-way valve 450 is fixed in place and cannot move within the barrel 410. In contrast, the piston 460 can move within the barrel in response to pressure. Put another way, the reaction chamber 430 is defined by the one-way valve 450, the barrel sidewall 412, and the piston 460.

The reaction chamber 430 can also be described as having a first end and a second end. The moveable piston 460 is at the first end 434 of the reaction chamber, while the one-way valve 450 is present at the second end 432 of the reaction chamber. In this illustration, the reaction chamber 430 is directly on one side of the piston 460, and the fluid chamber 440 is directly on the opposite side of the piston.

The reagent chamber 420 contains $H_2O_2$ and may optionally contain other materials such as a solvent (water, for example). The reaction chamber 430 contains at least one catalyst. The fluid chamber 440 contains the fluid to be delivered. As depicted here, the reagent chamber 420 contains a solvent 480, the reaction chamber 430 contains two different catalysts 482, 484, preferably in a dry powder form, and the fluid chamber 440 contains a fluid 486 (in some preferred embodiments, a high-viscosity fluid). Again, it should be noted that this figure is not drawn to scale. The chemical reagents, as illustrated here, do not fill up the entire volume of the reaction chamber. Instead, a head space 436 is present within the reaction chamber.

Each chamber has a volume, which in the depicted illustration is proportional to the height of the chamber. The reagent chamber 420 has a height 425, the reaction chamber 430 has a height 435, and the fluid chamber 440 has a height 445. In this illustrated embodiment, the volume of the reaction chamber is sufficient to contain the solvent and the two chemical reagents; however, in other embodiments, the reaction chamber can be smaller since the volume of the reagent chamber can be used for the reaction.

Activation switch 492 causes the heat activatable valve 450 to be opened, and the liquid 480 enters into the reaction chamber 430 and reacts over and/or dissolves the catalysts.

As the amount of gas increases, the pressure exerted on the piston 480 increases until, after reaching a threshold value, the piston 480 moves downward towards the bottom end 404 of the syringe. This causes the volume of the reaction chamber 430 to increase, and the volume of the fluid chamber 440 to decrease. This results in the fluid 486 in the fluid chamber being dispensed through the orifice.

Depressing the plunger 470 causes the one-way valve 450 to be opened, and the liquid 480 enters into the reaction chamber 430 and reacts over and/or dissolves the catalysts. After the plunger 470 is depressed and no further pressure is being exerted on the one-way valve, the one-way valve 450 closes. In particular embodiments, the barrel sidewall 412 at the lower end 424 of the reagent chamber may contain grooves or is otherwise shaped to capture the plunger 470. Put another way, the plunger 470 may cooperate with the lower end 424 of the reagent chamber 420 to lock the plunger in place after being depressed.

As the amount of gas increases, the pressure exerted on the piston 460 increases until, after reaching a threshold value, the piston 460 moves downward towards the bottom end 404 of the syringe. This causes the volume of the reaction chamber 430 to increase, and the volume of the fluid chamber 440 to decrease. This results in the fluid 486 in the fluid chamber being dispensed through the orifice. In some embodiments, the combined volume of the reaction chamber 430 and the fluid chamber remains constant, but the volume ratio of reaction chamber to fluid chamber 440 will increase as gas is generated in the reaction chamber. Note that the one-way valve 450 does not permit the gas 488 to escape from the reaction chamber into the reagent chamber.

FIG. 2 illustrates one embodiment of a system for delivering a fluid. It should be understood that the gas-powered fluid delivery system and methods of the invention are not limited to this embodiment but can be any design for gas-powered delivery of a fluid, as can be obtained or constructed by the workers skilled in this area without undue experimentation. For example, as mentioned above, the delivery systems may include any of the designs described by Bennison et al. in U.S. Pat. No. 10,046,116.

It is contemplated that a high-viscosity fluid can be dispensed using the propellant compositions of the present disclosure can be a solution, dispersion, suspension, emulsion, etc. The high-viscosity formulation may contain a protein, such as a monoclonal antibody or some other protein which is therapeutically useful. The protein may have a concentration of from about 150 mg/ml to about 500 mg/ml. The high-viscosity fluid preferably has an absolute viscosity of from about 5 centipoise to about 100,000 centipoise. In other embodiments, the high-viscosity fluid has an absolute viscosity of at least 40 centipoise, or at least 60 centipoise. The high-viscosity fluid may further contain a solvent or non-solvent, such as water, perfluoroalkane solvent, safflower oil, or benzyl benzoate.

The embodiment of the FIG. 2 described above has been illustrated as an auto-injector. Auto-injectors are typically held in the user's hand, have a cylindrical form factor, and have a relatively quick injection time of one second to 30 seconds. It should be noted that the concepts embodied in the above-described figures could also be applied to other types of injection devices, such as patch pumps. Generally, a patch pump has a flatter form factor compared to a syringe. Advantages to using a chemical gas-generating reaction in a patch pump include the small volume required, flexibility in the form/shape, and the ability to control the delivery rate. It is also contemplated, in alternate embodiments, that a catalyst is attached to the inner side of a plunger (opposite to the side that pushes against the fluid). Thus, when hydrogen peroxide contacts the inner side it decomposes to form gas that forces the plunger to reduce volume of the fluid chamber.

Suitable materials for the fluid delivery devices of the present disclosure are known in the art, as are methods for making the fluid delivery devices.

The force needed to activate the gas-generating chemical reaction can be far less than that required to activate a spring-driven device or to cock the spring in a spring-driven device. In addition, springs have a linear energy profile. The force provided by the gas-generating chemical reaction can be non-linear and non-logarithmic. The speed of the chemical reaction can be controlled by (i) adjusting the amount or particle size of the dry reagent (catalyst); (ii) changing the particle shape of the dry reagent; (iii) adjusting the packing of the dry reagent (catalyst); (iv) using mixing assist devices; (v) varying the concentration of $H_2O_2$; and/or (vi) altering the shape of the reaction chamber where the reagents are mixed and/or (vii) changing the concentration of a wet reagent.

Figure 3:
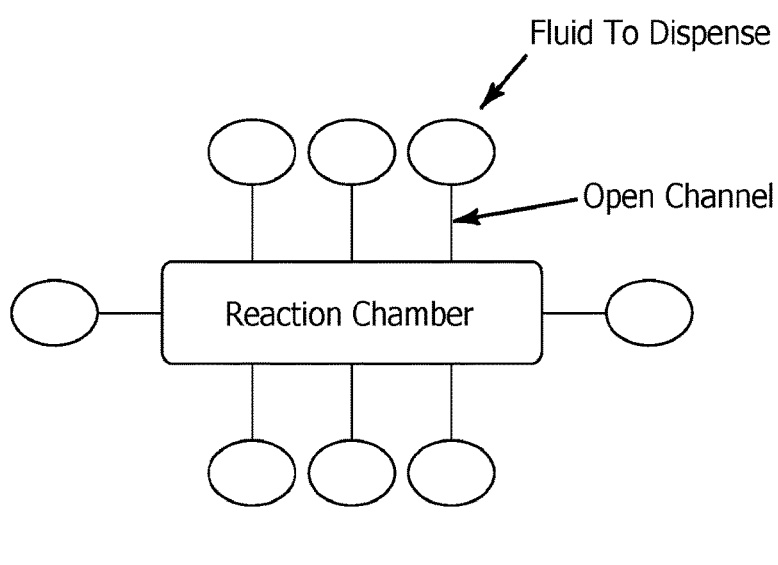
FIG. 3 schematically illustrates a fluid delivery system in which a single reaction chamber is connected via open channels to a plurality of fluid chambers.

The schematic illustration in FIG. 3 shows a rectangular chamber with rounded corners; however this first chamber can be of any shape and can be a flexible pouch without a clearly defined shape. This chamber may contain a reagent (hydrogen peroxide or one or more decomposition catalysts) The fluid to be dispensed is schematically shown in the filled ovals, the plurality of fluid chambers can be oval in cross-section or any shape. Each of the fluid chambers preferably contains a plunger (such as a flexible or expandable wall). In the illustration, fluid channels connect the first chamber with the plurality of fluid chambers. Typically, the fluid chambers each have an orifice through which the fluid flows out of the fluid chambers and a valve or a frangible barrier that retains the fluid until ready for use. In some embodiments, the fluid is a meltable solid and heat from the reaction melts the solid to a fluid prior to dispensing. The fluid channels can be open (so that all fluid chambers can be activated concurrently) or may contain valves so that the fluid chambers can be separately addressed (i.e., so that the fluid channels can be selectively opened). In some cases, the first chamber contains a fluid (the fluid can be a solution or suspension) comprising either hydrogen peroxide or a decomposition catalyst that, upon activation, flows into reaction chamber(s) (not shown) attached to each fluid chamber where the reaction occurs to push fluid out of the fluid chamber(s). Alternatively, the first chamber can be a reaction chamber in which, following activation, $H_2O_2$ and a decomposition catalyst are combined, generating a gas that forces fluid from one or more fluid chamber.

In some embodiments, the device contains a resistive heating element that is adapted to form a fluid connection between a reactant chamber and a reaction chamber. An activation switch is turned on to send an electric current through the heating element, generating a hot spot that forms the fluid connection, typically by melting a polymeric barrier between reactant chamber and reaction chamber; for example, the resistive heating element can be attached to a polymeric wall separating a reaction chamber and reactant chamber. In some embodiments, a reactant chamber (for example, filled with an aqueous $H_2O_2$ solution) is a collapsible vessel stored inside a reaction chamber that ejects reactant upon activation. In some preferred embodiments, the reaction chamber contains a fine catalyst powder (such as KI powder)—electrostatics cause the powder to coat all walls of the reaction chamber so that the reaction proceeds rapidly regardless of the orientation of the device.

FIG. 4 shows the initial (left) and final (right) schematics of a pouch squeezing dispenser 40. The pouch 44 is initially sealed with some force being exerted from the Dispenser onto the pouch. Once the Fluid Output Port 42 is opened (melted), the dispenser pushes the fluid out from the side away from the Port toward it, until all fluid has been expelled from the pouch. The schematic springs 46 can be springs or they can represent an elastomeric material (e.g. silicone, polyurethane, foam, rubber). An optional push plate 40 can be interposed between the spring mechanism 46 and the pouch. The reactant pouch 44 contains a reactant solution and when the fluid output port is opened, the fluid reactant is forced out of the reactant pouch into a reaction chamber where gas is generated to power the fluid delivery.

The springs may be, for example, a "chip clip" which is a spring-loaded clip that pinches the pouch. As an alternative to springs, magnets can apply the force that squeezes fluid from the pouch. In some embodiments, it is desirable that the springs do not deform the reaction chamber.

The hydrogen peroxide may be provided as an aqueous solution, preferably containing at least 10%, or at least 20%, or at least 50%, or from between 10 and 90%, or 10 and 80% $H_2O_2$ by mass. Desirably, neither the hydrogen peroxide chamber nor the catalyst chamber comprises a organics such as an organic solvent (for example, no alcohols and no aromatics or other organic liquids).

There are many catalysts that drive hydrogen peroxide decomposition, such as iron(III) chloride solution, manganese dioxide, copper(II) oxide, copper(II) sulfate, zinc oxide, and potassium iodide among others. The metal oxides are preferably present as dry powders. Water soluble catalysts such as potassium iodide, iron (III) chloride, catalase, $FeSO_4.7H_2O$ or $CuSO_4.5H_2O$, benzoic acid derivatives, $Mn(OH)_2$, ammonium hydroxide and iodine, haemase enzyme, metallic salts in quinoline/water, and NaOH can be provided in the catalyst chamber as solutions, and some as solid powders. In the case of powders, the hydrogen peroxide solution should be transferred into the catalyst chamber which then becomes the reaction chamber. In the case of catalyst solutions or suspensions, the catalyst solution can be mixed with the hydrogen peroxide solution.

Preferably, in some embodiments, the invention provides heating of a drug (or non-drug fluid) using the heat of reaction from hydrogen peroxide decomposition. Warming the fluid may provide a variety of advantages. For example, warming the drug (or other fluid) may increase patient comfort and decrease the viscosity of the drug (or other fluid) and allow for smaller needles or faster delivery time. Where the reaction chamber is adjacent to, or otherwise in thermal contact with the fluid chamber or any part of the fluid flow path (such as a needle), this configuration works to warm the fluid simultaneously as pressure is created.

The reactor and the fluid chambers will have intimate contact and good heat transfer to allow the heating to occur in a useful time scale. The fluid chamber wall is preferably thin, preferably 0.01 inch, or 0.005, or 0.001 inch or less, or from 0.001 to 0.1 inch. The fluid chamber may be designed to enhance heat transfer from the reaction chamber, at least in selected areas in which it is in direct contact with the reaction chamber and may contain a metal, polymer resin composite with a thermally-conductive filler, or other material which has high thermal conductivity. Since the reactor container can be a flexible pouch, it can be shaped around a rigid fluid chamber for maximum contact area. The flexible pouch can be comprised of a thermally conductive foil. In some embodiments, the fluid chamber is a glass drug vial. Preferably, a wall separating the fluid and reaction chambers comprises a substance having a thermal conductivity of at least 1 W/m·K. The fluid chamber may be comprised of two or more materials of varying thermal conductivity, for example, a relatively low thermal conductivity section comprising the plunger for expansion of the reaction chamber and/or compression of the fluid chamber; and a second region of the fluid chamber comprising a relatively high thermal conductivity; for example, a metallic (or other high thermal conductivity material) region that has no or little flexibility under the reaction conditions but provides for heat transfer into the fluid. In some preferred embodiments, the fluid is in direct contact with the surface for high thermal transfer.

In some preferred embodiments, that do not involve parenteral injection, the fluid remains in contact with a surface of the reaction chamber wall (for example, an expandable reaction chamber wall) so that, even after delivery to a surface, the fluid continues to be warmed after application to a surface. In some preferred embodiments, the ratio of (heated) reaction chamber wall to adjacent fluid flow path volume is in the range of 0.1 to 15, or 0.3 to 10, or 0.5 to 3 cm²/cc.

In some preferred embodiments, the flexible reaction chamber pouch can also be disposed around the injection needle or nozzle (or another fluid flow path). This increases the fluid's exposure to a warm surface as the surface area to drug volume increases in small diameter flow channels.

Delayed delivery: Some embodiments of the invention deliver a drug using a timed valve, or valve that opens at a desired temperature threshold. The delay valve between the reaction chamber and the fluid chamber could also be thermally activated. Phase change materials (PCM), such as ethylene-vinyl acetate, hexatcontane, paraffin wax, sorbitol, ammonium aluminum sulfate hexahydrate, or glutaric acid (among many others) are a solid at storage temperature, but melt to a fluid at an elevated temperature. This melting action of the valve material would open a channel between the reaction chamber and the fluid plunger and allow pressure to flow after the reaction has been initiated. The time of delay is a function of the heat capacity (Cp), latent heat (H), and volume of PCM relative to the heat of reaction of $H_2O_2$ decomposition. In another embodiment, a valve material (e.g. silicone, polyurethane, buna-n) could become more flexible at increased temperatures, thus flexing and opening a pressure pathway after being heated by the reaction. During the delay, heat from the reaction can heat up fluid in the fluid chamber(s).

The following examples are for purposes of further illustrating the present disclosure. The examples are merely illustrative and are not intended to limit processes or devices made in accordance with the disclosure to the materials, conditions, or process parameters set forth therein.

EXAMPLE

In one test, 0.3 mL liquid hydrogen peroxide was combined with 0.135 g KI resulting in 48.5 psi in less than 3 seconds, which is a substantially larger pressure and faster rate than a comparable reaction of bicarbonate with citric acid. The decomposition of hydrogen peroxide with a catalyst results in quickly producing liquid water, oxygen in the gas form, and heat. This reaction happens spontaneously and exothermically in the presence of a catalyst. The reaction initiates and will quickly warm once the exothermic reaction is initiated. In our experiments, we used aqueous $H_2O_2$ at room temperature. If the reaction is performed in a confined volume it quickly produces pressure due to both the evolution of oxygen and an increase in temperature. We have shown that the pressure created from this decomposition can quickly deliver viscous fluid through a small gauge needle in a time quicker than autoinjectors currently on the market. We found that 0.2 grams of 50% hydrogen peroxide can create more than 283 psi in a 2 mL reactor when exposed to a catalyst, which delivers 1 mL of 30 cP fluid through a 27 gauge thin wall needle in less than 2 seconds. We have found that dry metal oxides (for example, manganese dioxide) work well when their surface area is large, but the decomposition kinetics reduce by more than 100× once their surfaces are wet. We have also found that catalysts in solution (potassium iodide) complete the decomposition with fast kinetics.

Calculated Example

Many drugs in delivery devices are stored in the refrigerator. At the time of use, the user must take them out of the refrigerator and allow them to warm to room temperature for 30 minutes. This can be inconvenient and daunting for the user. The exotherm from the hydrogen peroxide decomposition reaction can decrease this time. The calculations below show how much warming we can expect from a ChemEngine utilizing hydrogen peroxide decomposition.

Reactant is 0.3 grams of 50 wt. % $H_2O_2$. This is 0.0044 mol of $H_2O_2$. The heat of reaction for $H_2O_2$ decomposition is 95.2 kJ/mol. 95.2 kJ/mol*0.0044 mol=0.42 kJ=420 J We assume that a drug delivery device holds 3 mL of drug that has water-like density and heat capacity. We calculate how much the drug can be heated by the reaction.

Drug heat capacity=4.18 J/(g° C.)
Volume of drug=3 mL
Density of drug=1 g/mL
Mass of drug=3 mL*1 g/mL=3 g
Starting temperature of the drug=5° C. (refrigerated)
The mass of fluid that is heated by the reaction includes reaction liquid, so 0.3 g+3.0 g=3.3 g
The rise in temperature due to the exotherm of the reaction: 420 J/3.3 g/4.18 J/g° C.=30.4° C.
Final temperature of drug is 5° C.+30.4° C.=35.4° C.
This final temperature is near body temperature (37° C.) and will be comfortable for the patient to inject.

What is claimed is:

1. A fluid flow system, comprising:
an activation switch;
an electrical power source connected to the activation switch;
a resistive heater attached to a first chamber;
an electrical connection from the power source to the resistive heater;
wherein the first chamber comprises a first reaction composition;
a second chamber comprising a second reaction composition;
wherein, if the first and second reaction compositions are combined, a gas is generated;
wherein the resistive heater is adapted to open a pathway in the first chamber that creates an open flow path between the first and second chambers;
the first chamber comprising at least one collapsible wall;
a fluid chamber comprising a fluid; and
a plunger adjacent the fluid chamber that is adapted to reduce volume of the fluid chamber when the gas is generated.

2. The system of claim 1 wherein the first chamber is made of a polymeric film.

3. The system of claim 1 wherein the first chamber is made of an elastic material that contracts as fluid is ejected from the chamber.

4. The system of claim 1 wherein the first chamber comprises a valve that melts or decomposes in response to the heat supplied by the resistive heater.

5. The system of claim 4 wherein the valve comprises a simple plug or patch of material.

6. The system of claim 1 wherein the first and second reaction compositions are fluid compositions that flow into an expansion chamber when the system is activated.

7. The system of claim 1 wherein the first chamber is an expansion chamber; or, alternatively, wherein the second chamber is an expansion chamber.

8. The system of claim 1 wherein the first and second reaction compositions each comprise one or more reactants and catalyst; or one of the first and second reaction compositions comprises a catalyst while the other composition comprises a compound that decomposes in the presence of the catalyst.

9. The system of claim 1 wherein one or more springs push against the first chamber.

10. The system of claim 1 wherein a single device comprises a plurality of first chambers either connected to a single second chamber or a plurality of second chambers.

11. The system of claim 10 wherein each first chamber comprises a resistive heater adapted to open a pathway in the first chamber.

* * * * *